United States Patent [19]

Morton et al.

[11] Patent Number: 5,413,793
[45] Date of Patent: May 9, 1995

[54] MULTIPHASE SUPPOSITORY

[75] Inventors: Oswald Morton, London, United Kingdom; Koral Embil, Istanbul, Turkey

[73] Assignee: EDKO Trading and Representation Company Limited, Istanbul, Turkey

[21] Appl. No.: 691,021

[22] PCT Filed: Dec. 29, 1989

[86] PCT No.: PCT/GB89/01545

§ 371 Date: Aug. 28, 1991

§ 102(e) Date: Aug. 28, 1991

[87] PCT Pub. No.: WO90/07324

PCT Pub. Date: Jul. 12, 1990

Related U.S. Application Data

[63] Continuation-in-part of Ser. No. 361,322, Jun. 5, 1989, abandoned.

[30] Foreign Application Priority Data

Dec. 30, 1988 [GB] United Kingdom ............. 8830407

[51] Int. Cl.⁶ .................... A61K 9/02; A61K 31/695
[52] U.S. Cl. .................................. 424/436; 514/63; 514/882; 514/966
[58] Field of Search .............. 514/63, 882, 966; 424/436, DIG. 15

[56] References Cited

U.S. PATENT DOCUMENTS

| | | |
|---|---|---|
| 2,727,846 | 12/1955 | Talbot . |
| 3,085,934 | 4/1963 | Vierling . |
| 3,098,795 | 7/1963 | Kreps . |
| 3,415,249 | 12/1968 | Sperti ............................ 514/966 |
| 3,881,012 | 4/1975 | Mima et al. ..................... 514/197 |
| 3,917,825 | 11/1975 | Matsuzawa et al. . |
| 4,198,390 | 4/1980 | Rider . |
| 4,812,480 | 3/1989 | Shirakura et al. ............... 514/557 |

FOREIGN PATENT DOCUMENTS

| | | |
|---|---|---|
| 828140 | 11/1969 | Canada . |
| 1991 | 9/1963 | France . |
| 2163352 | 12/1971 | France . |
| 2218086 | 2/1974 | France . |
| 2636756 | 8/1976 | Germany . |
| 6172716 | 4/1984 | Japan . |
| 914925 | 1/1963 | United Kingdom . |

OTHER PUBLICATIONS

Martindale, *The Extra Pharmacopoeia*, 1325–26 (1989).
Remington's Pharmaceutical Sciences, 15th Ed., Mack Publishing Co., Easton, Pa., USA, pp. 713–714 and 1546–1552 (1975).
Hara, Chemical Abstracts, vol. 105, No. 49069e (1986).

*Primary Examiner*—John Kight, III
*Assistant Examiner*—Jeffrey Mullis
*Attorney, Agent, or Firm*—Rothwell, Figg, Ernst & Kurz

[57] ABSTRACT

The invention provides a multiphase pharmaceutical composition for combatting an anorectal disease comprising at least one phase containing one or more medicaments for combatting said disease and at least one phase adapted for delayed release of a silicone oil whereby application of said composition at a region affected by said disease deposits said medicament or medicaments thereon and a layer of silicone oil is formed thereover, so protecting the medicaments from erosion by aqueous media.

7 Claims, 1 Drawing Sheet

MULTIPHASE SUPPOSITORY

CROSS-REFERENCE TO RELATED APPLICATION

This application is a continuation-in-part of U.S. patent application Ser. No. 07/361,322 filed Jun. 5, 1989, now abandoned.

This invention concerns pharmaceutical formulations for the treatment of anorectal diseases.

Anorectal diseases include haemorrhoids and anal fissures which are commonly treated with combinations of astringents, antiseptics, topical analgesics, vasoconstrictors, antispasmodics and antiinflammatory steroids. However, the healing of the lesions is commonly inhibited by the mucous environment which, for example, leads to maceration of moist perianal skin.

One possible solution to this problem would be to apply medicaments, for example to perianal lesions, in an occlusive layer which would repel water from the treated area. However, such conditions tend also to cause retention of fluids produced by the tissues, so that such an occlusive layer, by producing maceration of the affected area would thereby exacerbate the problem.

Furthermore, it is difficult to ensure that the occlusive layer does not form a barrier to prevent the medicaments from reaching the intended site of application.

On the other hand, at internal sites a deposited occlusive layer, for example of suppository base containing medicaments, is subject to erosion by aqueous media which can quickly reduce the beneficial effect of the medicament(s).

We have found that it is possible at least partially to overcome these problems by formulating medicaments for the treatment of anorectal diseases in a multiphase formulation wherein the medicaments reach the site of intended application first and a layer of silicone oil is released to cover the area to repel liquid water therefrom. Silicones possess the property of repelling liquid water but allowing the passage of water vapour, for example, water vapour formed by insensible perspiration from the skin.

We thus provide a multiphase pharmaceutical composition for combatting an anorectal disease comprising at least one phase containing one or more medicaments for combatting said disease and at least one phase adapted for delayed release of a silicone oil whereby application of said composition at a region affected by said disease deposits said medicament or medicaments thereon and a layer of silicone oil is formed thereover, so protecting the medicaments from erosion by aqueous media.

Figure 1:
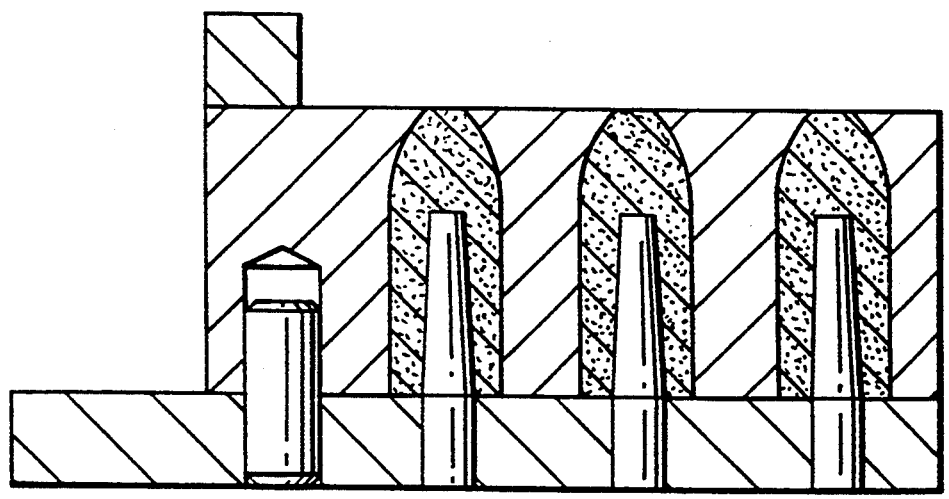
FIG. 1 is a cross sectional view of a mold for forming suppositories according to the invention.

In one embodiment of the invention, the composition comprises a cream containing the medicament(s) together with microcapsules containing silicone oil which rupture to release the silicone oil after application of the composition to the affected area.

The microcapsules may comprise silicone oil encapsulated in a material which ruptures (a) on application of pressure, (b) by melting at or just below body temperature, (c) by dissolving in body fluids or by any other means.

Capsules which rupture under pressure include NCR capsules.

Capsule materials which melt at close to body temperature include hard or soft gelatine.

Capsule materials which dissolve in body fluids include polymeric materials e.g. polymethacrylates such as Eudragit which dissolve at the pH of the gut.

The microcapsules may be in the size range 1 to 1000 microns.

The silicone oil will preferably be a polydialkylsiloxane oil, more preferably polydimethylsiloxane. Suitable medical grade silicone oils include Dow Corning 360 Medical Fluid.

The phase in which the medicament(s) are contained may be a conventional cream base, e.g. containing oily or waxy materials such as liquid paraffin, white petroleum or cetyl alcohol, water and one or more surfactants to produce a water-in-oil emulsion. A bactericide such as benzalkonium chloride is conveniently present.

Medicaments which may usefully be present include astringents such as bismuth subgallate, local anaesthetics such as benzocaine or lignocaine and antiinflammatory steroids such as hydrocortisone acetate.

According to a further embodiment of the invention, the composition takes the form of a suppository comprising an outer layer containing the medicament(s) in a suppository base surrounding one or more separate phases containing the silicone oil.

The medicaments and silicone oil may be as described above for the creams according to the invention.

The suppository base may, for example, be any conventional suppository base material such as glycogelatin, polyethylene glycol, fractionated palm kernel oil or, more preferably, one or more natural, synthetic or semi-synthetic hard fats such as cocoa butter. A particularly preferred material is one of the range of cocoa butter products sold under the trade name Witepsol by Dynamit Nobel, Slough, England.

The phase containing the silicone oil may comprise an inner core of a further suppository base having the silicone oil dispersed therein. It is important to achieve a phased melting and distribution with the medicaments phase melting first and reaching the lesion, followed by melting of the second phase allowing the medicaments on the lesion to be coated and protected by the silicone oil. In many cases, the melting point of the outer layer will advantageously be at least 1° C., preferably 2° C., lower than that of the inner core.

It may be preferable, however, for the silicone oil to be contained in liquid form in one or more capsules embedded in the outer layer of suppository base. Such capsules, as in the case of the microcapsules discussed above, may be designed to release the silicone oil by rupture achieved by pressure, dissolution or, more preferably melting. In the latter case, the capsule may be made from a material such as hard or soft gelatin having a melting point higher than that of the outer suppository base, in the same way as the inner core of suppository base discussed above.

The capsule(s) may comprise a single relatively large capsule or a number of smaller capsules dispersed within the outer suppository mass. The suppositories may be provided with a gauze attachment to assist location in the anorectal region.

Suppositories according to the invention can be made in any convenient way. Thus, for example, the outer suppository layer may be cast in conventional suppository moulds into which one or more pins or rods protrude longitudinally after solidification, the pins may be removed, the moulds may be inverted and the phase containing the silcone oil introduced into the cavity left by removal of the pins. If the material so introduced does not fill the cavities completely, the remainder of the space can advantageously be filled with further suppository base material to ensure that the silicone oil-containing phase is completely surrounded by suppository base material.

The cavities referred to above may be filled with the second suppository base material as previously described or with one or more of the above-mentioned capsules.

The following Examples are given by way of illustration only:

EXAMPLE 1 CREAM

|  | % |
|---|---|
| Dow Corning 360 silicone oil (dimethasone) encapsulated in pressure sensitive NCR microcapsules | 10 |
| Liquid paraffin | 22.75 |
| White petrolatum | 8.0 |
| Cetyl alcohol | 7.0 |
| Span 60 | 3.0 |
| Benzocaine | 2.5 |
| Bismuth subgallate | 2.0 |
| Potassium dihydrogen phosphate | 0.5 |
| 1% Aqueous Benzalkonium chloride | 10.0 |
| Tween 60 | 5.0 |
| 70% Aqueous sorbitol | 5.0 |
| Hydrocortisone acetate | 0.5 |
| Water | 23.75 |

The oily phase comprising the liquid paraffin, white petrolatum, cetyl alcohol and Span 60 are mixed at 60°. The aqueous phase comprising the remaining components except the microcapsules is also blended at 60° C. and the two phases combined and blended. The microcapsules are added subsequently and dispersed throughout the cream.

EXAMPLE 2 SUPPOSITORY

| | |
|---|---|
| Dow Corning 360 silicone oil (dimethasone) encapsulated in 50 soft gelatin capsules m.p. 36° C. | 10 g |
| Bismuth subgallate | 2.0 g |
| Benzocaine | 2.5 g |
| 50% Benzalkonium chloride | 0.2 g |
| Hydrocortisone acetate | 0.5 g |
| Witepsol S55 suppository base | 72.15 g |
| Witepsol E85 suppository base | 12.65 g |

The above components apart from the encapsulated silicone oil are blended at 55° C., cooled to 40° C. and poured into 50 moulds as shown in FIG. 1 hereinafter. The pin of the mould is of the same diameter as the silicone oil capsules. After cooling, the pins are withdrawn, the moulds are inverted and one capsule inserted in the cavity left by each pin. The remainder of the cavity is filled with a blend of the two Witepsol bases at 40° C. After chilling, the suppositories are removed from the moulds and packaged.

We claim:

1. A multiphase pharmaceutical composition for combatting an anorectal disease comprising a first phase containing a medicament for combatting said disease and a second phase adapted for delayed release of a silicone oil whereby application of said composition at a region affected by said disease deposits said medicament thereon and a layer of silicone oil is formed thereover, so protecting the medicament from erosion by aqueous media, wherein said composition is in the form of a suppository comprising an outer layer containing said medicament in a suppository base surrounding one or more separate phases containing the silicone oil.

2. A composition as claimed in claim 1 in which the silicone oil is a polydialkylsiloxane.

3. A composition as claimed in claim 1 in which said medicament is selected from the group consisting of astringents, local anaesthetics and antiinflammatory steroids.

4. A composition as claimed in claim 1 in which the suppository base comprises one or more natural, synthetic or semi-synthetic hard fats.

5. A composition as claimed in claim 1 wherein the silicone oil is contained in liquid form in one or more capsules embedded in the outer layer of suppository base.

6. A multiphase pharmaceutical composition for combatting an anorectal disease comprising a first phase containing a medicament for combatting said disease and a second phase adapted for delayed release of a liquid consisting essentially of silicone oil whereby application of said composition at a region affected by said disease deposits said medicament thereon and a layer of silicone oil is formed thereover, so protecting the medicament from erosion by aqueous media, wherein said composition is in the form of a cream containing said medicament together with microcapsules containing silicone oil which rupture to release the silicone oil after application of the composition to the affected region.

7. A composition as claimed in claim 6 in which the cream is a water-in-oil emulsion.

* * * * *